United States Patent
Lee et al.

(10) Patent No.: US 8,637,003 B2
(45) Date of Patent: Jan. 28, 2014

(54) TREATING MULTIPLE SYSTEM ATROPHY WITH HMSC

(75) Inventors: Phil Hyu Lee, Gyeonggi-do (KR); Oh Young Bang, Seoul (KR); Young Hwan Ahn, Gyeonggi-do (KR)

(73) Assignee: Ajou University Industry-Academic Cooperation Foundation, Gyeonggi-do (KR)

( * ) Notice: Subject to any disclaimer, the term of this patent is extended or adjusted under 35 U.S.C. 154(b) by 1636 days.

(21) Appl. No.: 12/081,880

(22) Filed: Apr. 23, 2008

(65) Prior Publication Data

US 2009/0269311 A1    Oct. 29, 2009

(51) Int. Cl.
*C12N 5/00* (2006.01)
(52) U.S. Cl.
USPC .......................................... 424/93.7; 435/366
(58) Field of Classification Search
None
See application file for complete search history.

(56) References Cited

PUBLICATIONS

On Koc et al. Bone Marrow Transplantation (2002) 30. pp. 215-222.*
Lee, PH, et al.,"Autologous Mesenchymal Stem Cell Therapy Delays the Progression of Neurological Deficits in Patients with Clinical Multiple System Atrophy", *Clinical Pharmacology & Therapeutics*,83, 5, pp. 723-730, (2008).
Jin, H. K., et al.,"Intracerebral transplantation of mesenchymal stem cells into acid sphingomyelinase-deficient mice delays the onset of neurological abnormalities and extends their life span", *The Journal of Clinical Investigation*, vol. 109, No. 9, pp. 1183-1191, (May 2002).
Mazzini, L., et al.,"Stem Cell therapy in amyotrophic lateral sclerosis: a methodological approach in humans", *Amyotroph Lateral. Scler. Motor Neuron Disord.*, vol. 4, pp. 158-161, (2003).
Bang, O. Y., et al.,"Autologus Mesenchymal Stem Cell Transplantation in Stroke Patients", *Ann Neurol.* vol. 57 pp. 874-882, (2005).
Geser, F., et al., "Progression of Multiple System Atrophy (MSA): A Prospective Natural History Study by the European MSA Study Group (EMSA SG)", *Movement Disorders*, vol. 21, No. 2, pp. 179-186, (2006).
Paviour, D.C., et al.,"Longitudinal MRI in progressive supranuclear palsy and multiple system atrophy: rates and regions of atrophy", *Brain*, vol. 129, pp. 1040-1049, (2006).
Barry, F.P., et al.,"Mesenchymal stem cells: clinical applications and biological characterization", *The Int. J. Biochem. & cell Biology*, vol. 36, pp. 568-584, (2004).
Bae, J.S. et al.,"Bone Marrow-Derived Mesenchymal Stem Cells Promote Neuronal Networks with Functional Synaptic Transmission After Transplantation into Mice with Neurodegeneration", *Stem Cells*, vol. 25 pp. 1307-1316, (2003).
Amar, A.P., et al.,"Endovascular Restorative Neurosurgery: A Novel Concept for Molecular and Cellular Therapy of the Nervous System", *Neurosurgery*, vol. 52, No. 2, pp. 402-413, (Feb. 2003).
McRae, C., et al.,"Effects of Perceived Treatment on Quality of Life and Medical Outcomes in a Double-blind Placebo Surgery Trial", *Arch Gen Psychiatry*, vol. 61, pp. 412-420, (Apr. 2004) & correction,vol. 61, p. 627, (Jun. 2004).

* cited by examiner

*Primary Examiner* — Blaine Lankford
(74) *Attorney, Agent, or Firm* — Vorys, Sater, Seymour and Pease LLP; Mihsun Koh

(57) ABSTRACT

The present invention provides a method for treating multiple system atrophy, comprising administering a therapeutically effective amount of mesenchymal stem cells (MSCs) to a human in need thereof. Preferably, the administering is performed by an intra-arterial injection of said MSCs and one or more intravenous injections of said MSCs.

7 Claims, 7 Drawing Sheets

TREATING MULTIPLE SYSTEM ATROPHY WITH HMSC

FIELD OF THE INVENTION

The present invention relates to a method for treating multiple system atrophy, and more particularly, to a method for treating multiple system atrophy comprising administering a therapeutically effective amount of mesenchymal stem cells (MSCs) to a human in need thereof.

DESCRIPTION OF THE RELATED ART

Multiple system atrophy (MSA) is a sporadic, progressive, adult-onset neurodegenerative disorder associated with varying degrees of parkinsonism, autonomic dysfunction, and cerebellar ataxia, characterized pathologically by asynuclein-positive glial cytoplasmic inclusions in brain and spinal cord. As disease progression in MSA is much faster and no drug treatment consistently benefits MSA patients in the long-term, neuroprotective or regenerative strategies are inevitable in the management of MSA patients.

Mesenchymal stem cells (MSCs) are present in adult bone marrow and represent <0.01% of all nucleated bone marrow cells. MSCs are themselves capable of multipotency, with differentiation under appropriate conditions into chondrocytes, skeletal myocytes, and neurons. Many clinical and animal studies of MSC transplantation have focused on ischemic conditions, such as ischemic heart disease or ischemic strokes, making a contribution to improvement of functional recovery. Clinically, cell therapy with MSCs is particularly attractive because autologous transplantation is possible; MSCs are easily obtained from the patient's own cells, can be expanded in culture, and then reintroduced into the patient. In addition, there are no ethical issues with the use of MSCs.

However, the application of MSCs in neurodegenerative diseases is seldom studied. Jin et al. reported that intracerebral transplantation of MSCs had significant effects on the progression of neurological deficits and lifespan in a knock-out mouse model of Niemann-Pick disease, a lysosomal storage disorder showing progressive ataxia and Purkinje cell loss (Jin, H. K., Carter, J. E., Huntley, G. W. & Schuchman, E. H. (2002) Intracerebral transplantation of mesenchymal stem cells into acid sphingomyelinase-deficient mice delays the onset of neurological abnormalities and extends their life span. *J. Clin. Invest.* 109, 1183-1191). In a study of MSC transplantation into the spinal cord of patients with amyotrophic lateral sclerosis, Mazzini et al. reported that most patients showed a slowing down of the linear decline or an increase in the muscle strength (Mazzini, L. et al. (2003) Stem cell therapy in amyotrophic lateral sclerosis: a methodological approach in humans. *Amyotroph. Lateral. Scler. Motor Neuron Disord.* 4, 158-161).

SUMMARY OF THE INVENTION

In this regard, while testing the feasibility and safety of cell therapy with MSCs through intra-arterial and repeated intravenous injection in patients with MSA and compared the long-term prognosis between MSC-treated and control patients, the present inventors have found that a certain MSC therapy in patients with MSA is safe and delayed the progression of neurological deficits with achievement of functional improvement in the follow-up period.

Therefore, the present invention provides a method for treating multiple system atrophy comprising administering a therapeutically effective amount of mesenchymal stem cells (MSCs) to a human in need thereof.

BRIEF DESCRIPTION OF THE DRAWINGS

The above and other features and advantages of the present invention will become more apparent by describing in detail exemplary embodiments thereof with reference to the attached drawings in which:

FIG. 1A is Mean (±SE) change from baseline in the unified multiple system atrophy rating scale (UMSARS) scores for MSC-treated and control patients throughout the 12 months of follow-up. FIG. 1B is UMSARS I analysis between MSC-treated and control patients. In FIGS. 1A and 1B, black squares mean MSC-treated patients and gray triangles mean control patients.

In FIGS. 2A to 2F, black squares mean MSC-treated patients and gray triangles mean control patients. *$P<0.05$ between the MSC and control groups using the Mann-Whitney U-test.

FIG. 4A shows increased FDG uptake on follow-up scan compared to baseline in five patients treated with MSCs. FIG. 4A shows decreased FDG uptake on the follow-up scan compared to the baseline in control patients. The mean follow-up period was 11.9 and 12 months in the MSC and control groups, respectively. Projections are on a three-dimensional standard brain (left side) and on standardized magnetic resonance imaging templates (right side).

DETAILED DESCRIPTION OF THE INVENTION

Figure 1A:
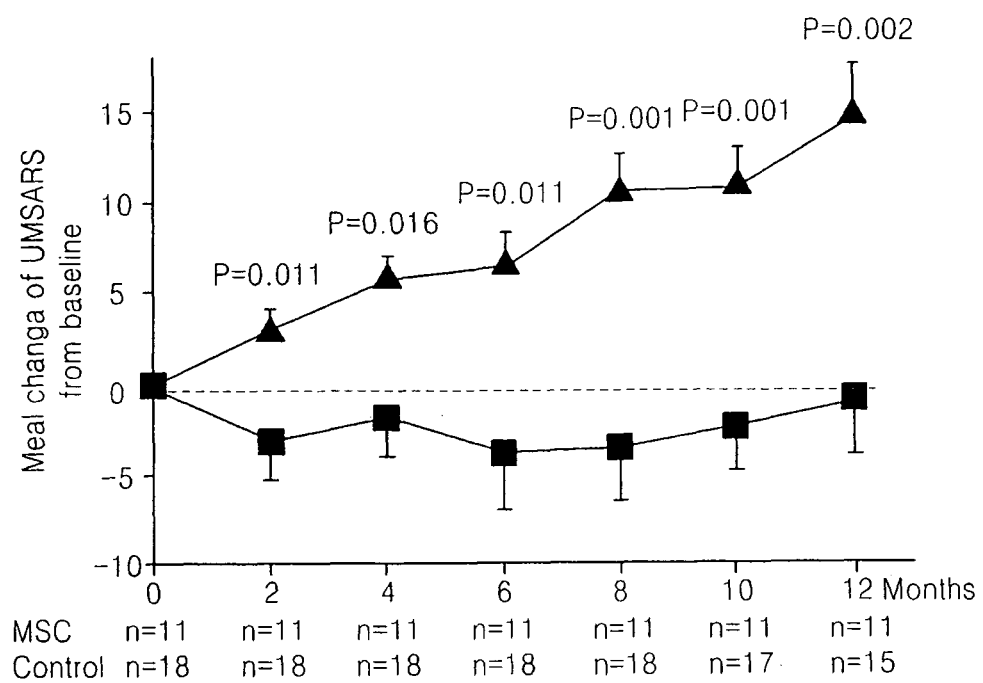
FIGS. 1A and 1B show the change of clinical rating scale scores from baseline.

The present invention provides a method for treating multiple system atrophy comprising administering a therapeutically effective amount of mesenchymal stem cells (MSCs) to a human in need thereof.

According to an aspect of the present invention, there is provided a method for treating multiple system atrophy, comprising administering a therapeutically effective amount of mesenchymal stem cells (MSCs) to a human in need thereof, wherein the administering is performed by an intra-arterial injection of said MSCs and one or more intravenous injections of said MSCs.

In the method of the present invention, MSCs may be derived from various species, preferably from a human. More preferably, autologous human-derived MSCs can be used in the method of the present invention. An embodiment of the present invention utilizes isolated and culture-expanded mesenchymal stem cells. MSCs can be isolated, purified, and expanded in culture, i.e. in vitro, to obtain sufficient numbers of cells for use in the methods described herein. See, Bang, O. Y., Lee, J. S., Lee, P. H. & Lee, G. (2005) Autologous mesenchymal stem cell transplantation in stroke patients. *Ann. Neurol.* 57, 874-882.

Thus in an embodiment, the subject human mesenchymal stem cells are obtained from the bone marrow or other mesenchymal stem cell source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood. Although in a preferred embodiment the mesenchymal stem cells are culturally expanded prior to use, it is also possible to use such mesenchymal stem cells without culture expansion. For example, mesenchymal stem cells may be derived from bone marrow and used after separation of blood cells therefrom, without expansion. Thus, for example, bone marrow may be enriched in human mesenchymal stem cells by removal of blood cells, and introduced into a patient in need thereof.

In a preferred embodiment, the intra-arterial injection is performed by infusing MSCs into a bilateral internal carotid artery and/or into a dominant vertebral artery. For example, the intra-arterial injection is performed by infusing MSCs in an amount of about $4 \times 10^7$ cells, more preferably about $2 \times 10^7$ cells into a bilateral internal carotid artery and about $2 \times 10^7$ cells into a dominant vertebral artery. The infusion time is 60 minutes. Each infusing may be carried out separately or at the same time. The infusion time may be about 60 minutes. It would be understood that said dosage of intra-arterial injection may be changed according to the conditions of a disease.

In a preferred embodiment, the intravenous injections are consecutively performed every month, beginning 1 month after the intra-arterial injection. Preferably, the intravenous injections are consecutively performed every month for 3 months, beginning 1 month after the intra-arterial injection. Each intravenous injection may be performed by infusing MSCs in an amount of about $4 \times 10^7$ into an antecubital vain for about 30 minutes. It would be understood that said dosage of intravenous injection may be changed according to the conditions of a disease.

For intra-arterial injection and intravenous injections of MSCs, said MSCs may be applied in dispersions (suspensions) and/or solutions including a pharmaceutically acceptable carrier, e.g., sterilized water, a buffer (about pH 7), or physiological saline. When needed, the dispersions and/or solutions may include a conventional additive, e.g., a preservative or a stabilizer.

The present invention will be described in further detail with reference to the following examples. These examples are for illustrative purposes only and are not intended to limit the scope of the present invention.

EXAMPLES

1. Methods (1) Data Collection.

Consecutive patients with MSA were recruited at Ajou University Hospital, Korea. All the patients were diagnosed as a probable MSA, according to the consensus criteria for clinical diagnosis of MSA. Patients were randomly allocated to the MSC or control group depending on treatment with MSCs, by use of a randomization table. After the initial allocation of patients to groups, study procedures were not blinded. Clinical assessments were made at baseline and at 2-month intervals for 12 months using the unified multiple system atrophy rating scale (UMSARS), which comprised four parts, including a historical review of disease-related impairments (Part I, 12 items), motor examination (Part II, 14 items), autonomic examination (Part III), and global disability scale (Part IV). UMSARS scores were obtained as the mean of scores performed by two independent investigators. The study protocol and consent form were approved by the Institutional Review Board for Human Investigation of Ajou University Hospital. We obtained written informed consent from all patients.

(2) Isolation of MSCs and Cell Preparation for Transplantation.

MSC preparation was performed using our previously reported method (Bang, O. Y., Lee, J. S., Lee, P. H. & Lee, G. (2005) Autologous mesenchymal stem cell transplantation in stroke patients. *Ann. Neurol.* 57, 874-882). Briefly, 5 ml of bone marrow was aspirated from the posterior iliac crest of patients in the MSC group. Bone marrow mononuclear cells were isolated using Ficoll density centrifugation. Mononuclear cells ($1 \times 10^6$/ml) were placed in a 175 cm² flask (Falcon, Franklin Lakes, N. J.) and cultured in low-glucose Dulbecco's modified Eagle's medium (Gibco-BRL, Grand Island, N.Y.) containing 10% fetal bovine serum (Hyclone, Irvine, Calif.), and 1% penicillin-streptomycin (Sigma, St Louis, Mo.) in a humidified incubator at 37° C. under 5% $CO_2$. After 5 days, nonadherent cells were removed by replacing the medium. Attached cells developed into colonies within 5-7 days. When these primary cultures of MSCs reached 80% confluence, the cells were harvested using 0.25% trypsin and subcultured. The autologous MSCs were culture expanded to reach $1 \times 10^8$ cells/patient. Every harvest of MSCs showed a homogenous population of cells with high expression levels of SH antigens (>93% of cells) and no expression of CD34, CD45, human leukocyte antigen-D related, or class I human leukocyte antigen (data not shown). Cell viability evaluated by Trypan blue staining at the end of the harvest and before infusion was >95% for every infusate. No evidence of bacterial, fungal, viral, or mycoplasmal contamination was observed in any of the flasks that tested weakly. The procedure for MSC preparation was performed under GMP (Good Manufacturing Practice) conditions (FCB-Pharmicell, Sungnam, South Korea).

Freshly harvested MSCs were resuspended in 100 ml of saline and were infused into patients through the infusion pump along with a running infusion of saline through a peripheral catheter. For the intra-arterial injection of MSCs, patients were brought to the angiography suite, placed in the supine position, and prepared and draped in a standard manner. Percutaneous access was obtained via the right femoral artery and a 6-Fr sheath was inserted. A 6-Fr guiding catheter (Guider, Target Therapeutics, Fremont, Calif.) was advanced into the cervical portion of the internal carotid artery and the proximal portion of vertebral artery, and $4 \times 10^7$ MSCs were injected slowly over 60 min ($2 \times 10^7$ in the bilateral internal carotid artery and $2 \times 10^7$ in the dominant vertebral artery). During the procedure, the catheter was connected to a continuous heparinized saline flush. For intravenous injection, $4 \times 10^7$ MSCs were infused slowly into an antecubital vein over 30 min. Beginning 1 month after the intra-arterial injection, intravenous injections were consecutively performed every month for 3 months so that the MSC-treated patients received $16 \times 10^7$ cells in total.

(3) PET Images.

PET/computed tomography data were acquired on a Discovery ST scanner (General Electric Medical Systems, Milwaukee, Wis.). After fasting at least 4 h, patients received 300 MBq of 18-FDG intravenously. All the subjects were instructed to rest comfortably for 30 min and the image acquisition was started. They first had a computed tomography scan (tube rotation time of 1 s per revolution; 120 kV; 70 mA; 5.0 mm per rotation and an acquisition time of 11.8 s for a scan length of 150.42 mm) and subsequently, one frame (8 min per frame) of emission PET data was acquired in a three-dimensional mode. PET images were reconstructed by iterative reconstruction (ordered-subsets expectation maximization with one iteration and 32 subsets) using the computed tomography images for attenuation correction.

(4) Statistical Parametric Mapping and SISCOM Analysis of Baseline and Follow-Up PET Images.

Baseline and follow-up FDG-PET images were spatially normalized to a standard template provided by Statistical Parametric Mapping 2 (Institute of Neurology, University of London, UK) on MATLAB software version 7.1 (Mathworks, Natick, Mass.). The normalized data were smoothed with a Gaussain kernel (full-width at half-maximum, 16 mm) to increase the signal-to-noise ratio and registered with the Talairach system of coordinates. To identify brain regions in which metabolic activity had changed after MSC therapy, baseline and follow-up PET images were compared with voxel-by-voxel manner (paired t-test). An uncorrected Po0.05 and extent threshold (Ke) more than 100 were considered to be significant. We analyzed the change in metabolic activity of control patients using the same method. To evaluate the metabolic change in individual patients, we performed subtraction analysis between baseline and follow-up images using the SISCOM software incorporated into Statistical Parametric Mapping 2.

(5) Assessment of Adverse Effects.

According to our protocol for adverse effects, we assessed the safety of intra-arterial and intravenous MSC infusion based on the development of an immediate or a delayed reaction. Immediate reactions included allergic reactions (tachycardia, fever, skin eruption, leukocytosis), local complications (hematoma, local infection at the site of bone marrow aspiration), vascular obstruction (tachypnea, oliguria, peripheral vascular insufficiency, or stroke), and systemic complications (systemic infections, increased aspartate aminotransferase and alanine aminotransferase, or blood urea nitrogen/creatinine levels). We performed diffusion-weighted MR images 1 day after the intra-arterial injection of MSCs to evaluate any ischemic lesions that may be associated with MSC infusion or angiographic complications. To evaluate tumor formation as a delayed reaction, we conducted a physical evaluation, a visual inspection of the skin and oral mucosa, and PET imaging.

(6) Statistical Analysis.

The statistical analysis of efficacy was based on the change of UMSARS at 2-month intervals for 12 months between the two groups. The Mann-Whitney U-test was used to examine the intentional difference between the two groups (the change in UMSARS including each part of the UMSARS and individual items in each part of the UMSARS, age at baseline, age at onset, disease duration, and PET scan interval). Fisher's exact test was used to compare categorical variables (sex and subtype of MSA). All statistical tests were two-sided, and P-values<0.05 were considered statistically significant using a commercially available software package (SPSS, version 10.0).

2. Results

We prospectively enrolled 29 patients with MSA of whom 11 received cell therapy with MSCs (MSC group) and 18 did not (control group). The clinical characteristics of the MSC and control groups are summarized in Table 1.

TABLE 1

| | Demographic characteristics at baseline | | | | |
|---|---|---|---|---|---|
| | Control group | | MSC group | | |
| | Whole | 30 < UMSARS ≤ 65 | Whole | 30 < UMSARS ≤ 65 | P-value |
| Patients (n) | 18 | 14 | 11 | 5 | NS*,† |
| Age (years) | 57.2 ± 6.5 | 57.3 ± 6.7 | 57.5 ± 6.5 | 54.8 ± 6.5 | NS*,† |
| Age at onset (years) | 53.2 ± 6.3 | 54.3 ± 7.1 | 51.9 ± 6.7 | 48.6 ± 5.6 | NS*,† |
| Sex (female, %) | 6 (33.3) | 7 (50) | 3 (27.3) | 3 (60) | NS*,† |
| Disease duration (years) | 4.0 ± 1.2 | 4.2 ± 1.2 | 5.8 ± 1.2 | 5.6 ± 1.5 | 0.001*, NS*,† |
| MSA-C/-P | 15/3 | 11/3 | 9/2 | 4/1 | NS*,† |
| UMSARS | 39.1 ± 14.0 | 44.3 ± 11.9 | 71.6 ± 19.8 | 52.5 ± 10.1 | <0.001*, NS*,† |
| PET scan interval | 12.0 ± 0.9 | | 11.9 ± 0.9 | | NS |

In table 1, MSA-C/-P means multiple system atrophy-cerrebellar/-parkinsonian; MSC means mesenchymal stell cell; NS means "not significant"; PET means positron emission tomography; UMSARS means Unified Multiple System Atrophy Rating Scale.
± values are means ± SD.
*Comparison of all the patients between the control and MSC groups.
†Comparison of the patients whose baseline UMSARS score ranged from 31 to 65 between the control and MSC groups.

In table 1, MSA-C/-P means multiple system atrophy-cerebellar/-parkinsonian; MSC means mesenchymal stem cell; NS means "not significant"; PET means positron emission tomography; UMSARS means Unified Multiple System Atrophy Rating Scale. ±values are mean±SD. *Comparison of all the patients between the control and MSC groups. †Comparison of the patients whose baseline UMSARS score ranged from 31 to 65 between the control and MSC groups.

The age at baseline, age at onset, and sex ratio were not significantly different between the two groups. The disease duration was longer in the MSC group than in the control group (P=0.001). The distribution of MSA subtypes was not different between the two groups; 15 MSA-C (cerebellar type) and 3 MSA-P (parkinsonian type) were in the control group, and nine in MSA-C and two MSA-P patients in the MSC group. The baseline Unified MSA Rating Scale (UMSARS) score was significantly higher in the MSC group than in the control group (P<0.001).

Figure 1B:
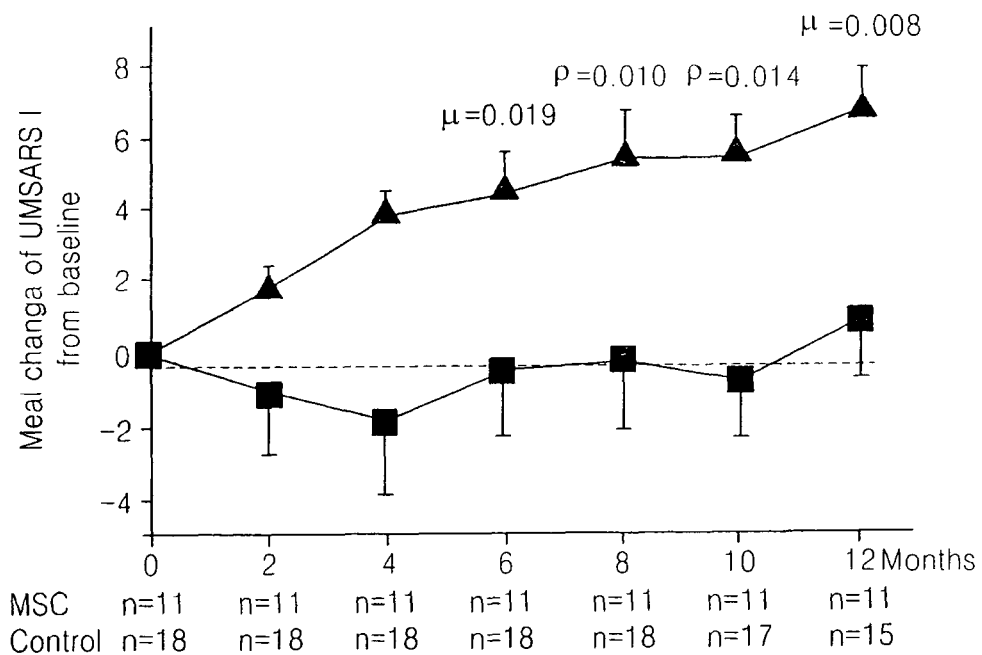
Figure 2A:
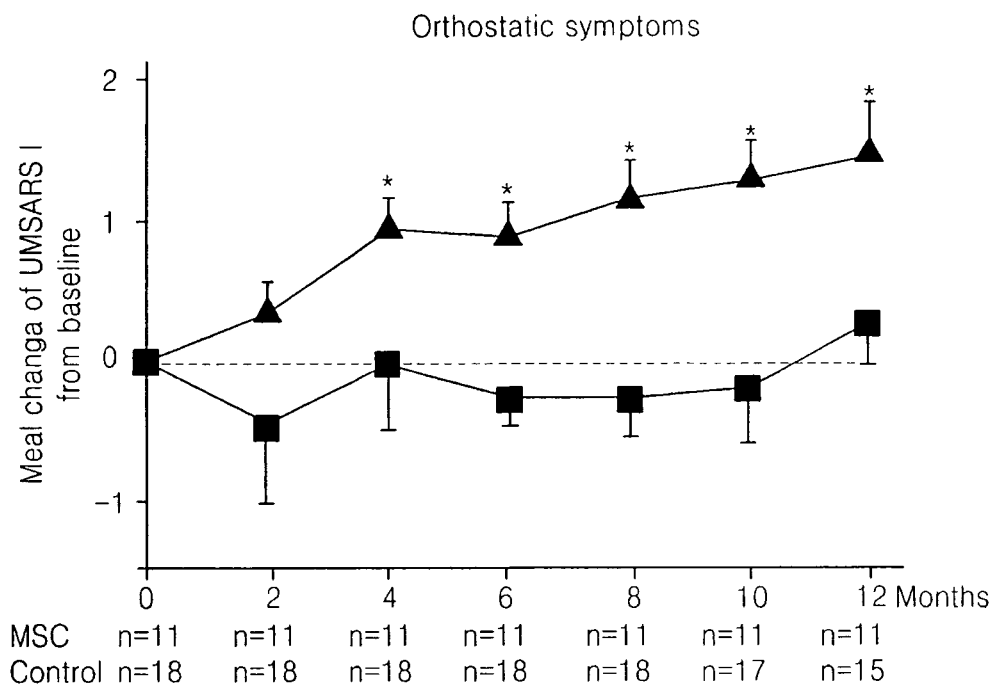
FIGS. 2A to 2F show analysis results of the individual items in each part of the unified multiple system atrophy rating scale (UMSARS) between mesenchymal stem cell (MSC)-treated and control patients. Orthostatic symptoms in UMSARS I items and finger tapping, rapid alternating movements, arising from chair, leg agility, and posture among UMSARS II items were statistically different in favor of MSC treatment compared with controls.
Figure 2B:
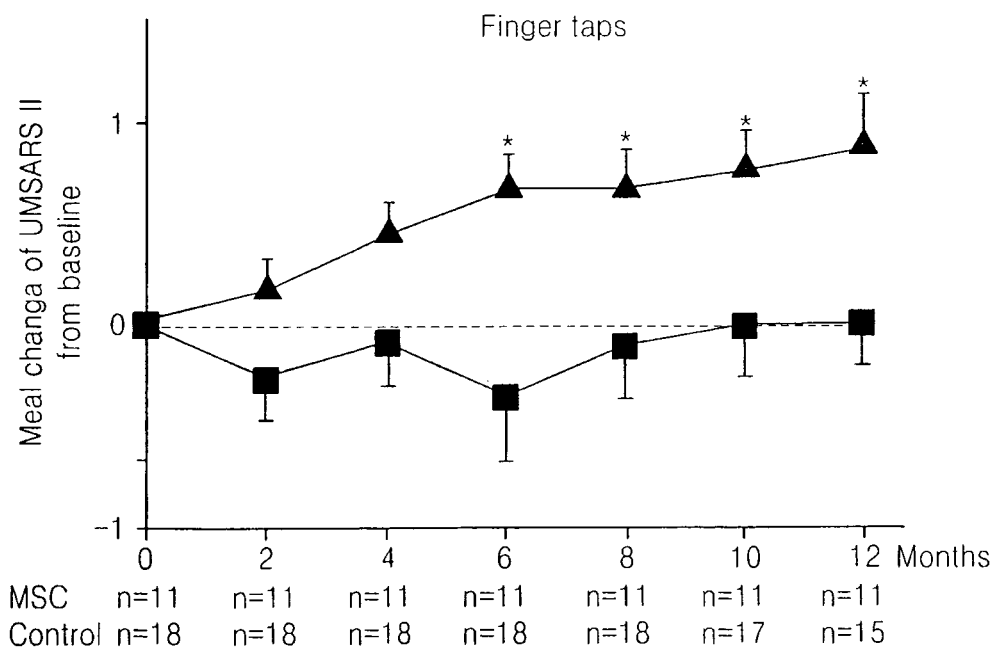
Figure 2C:
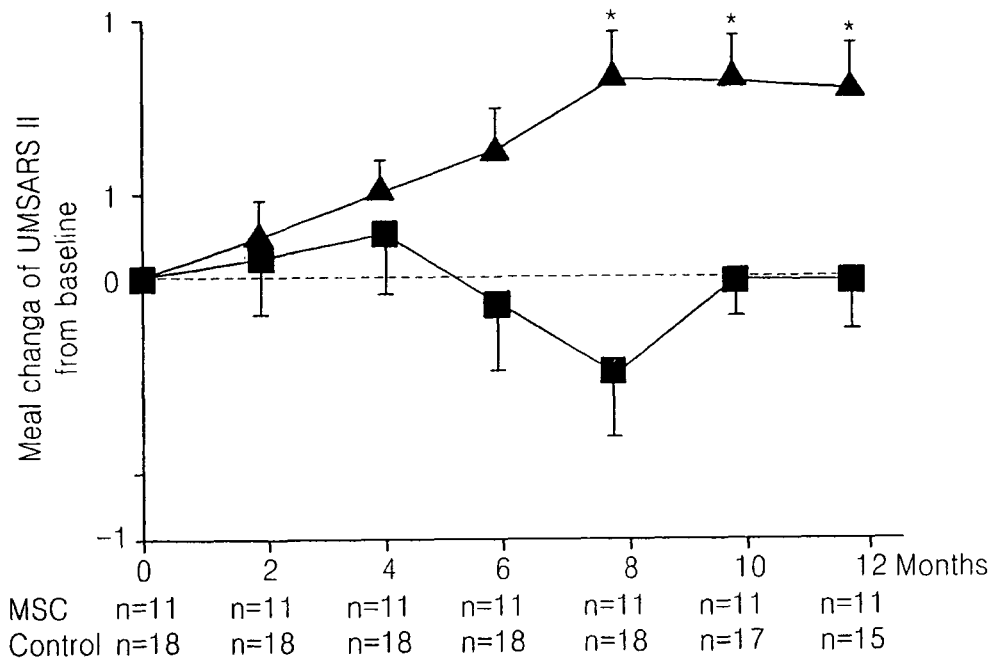
Figure 2D:
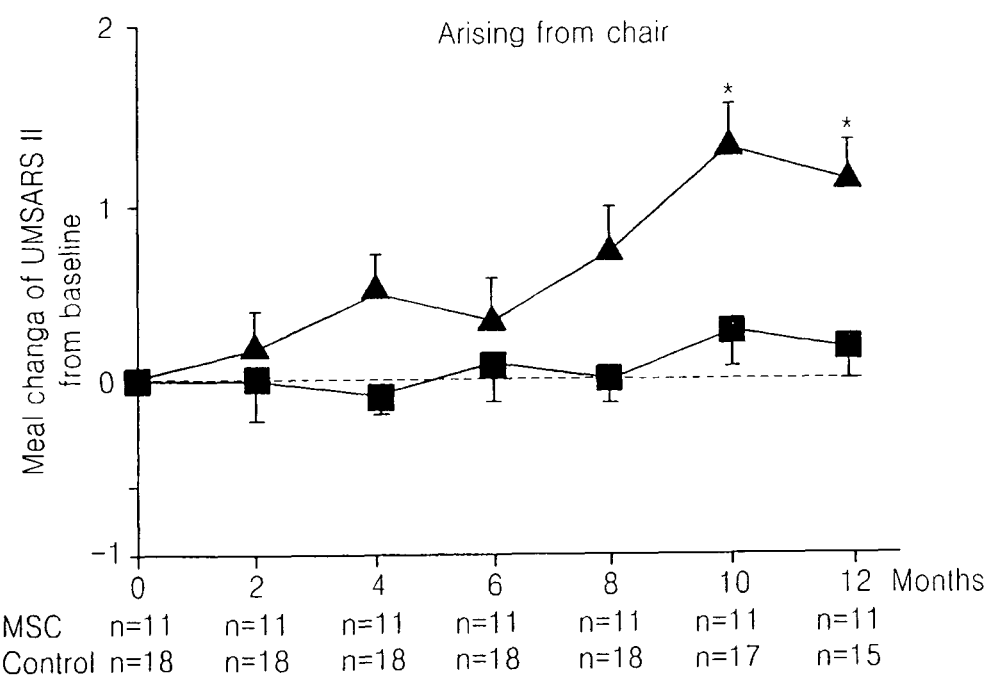
Figure 2E:
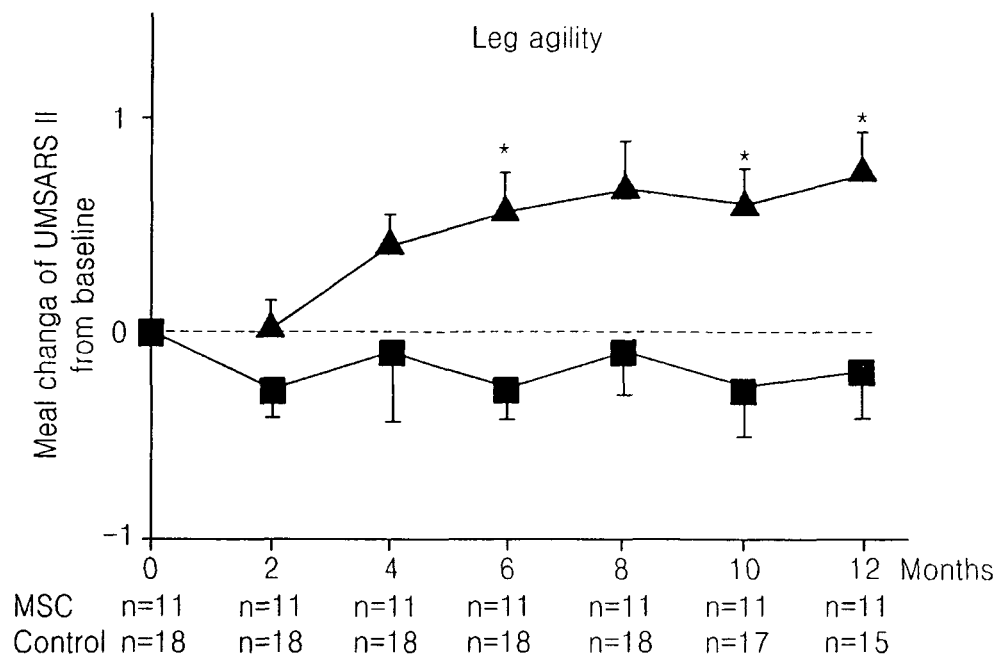
Figure 2F:
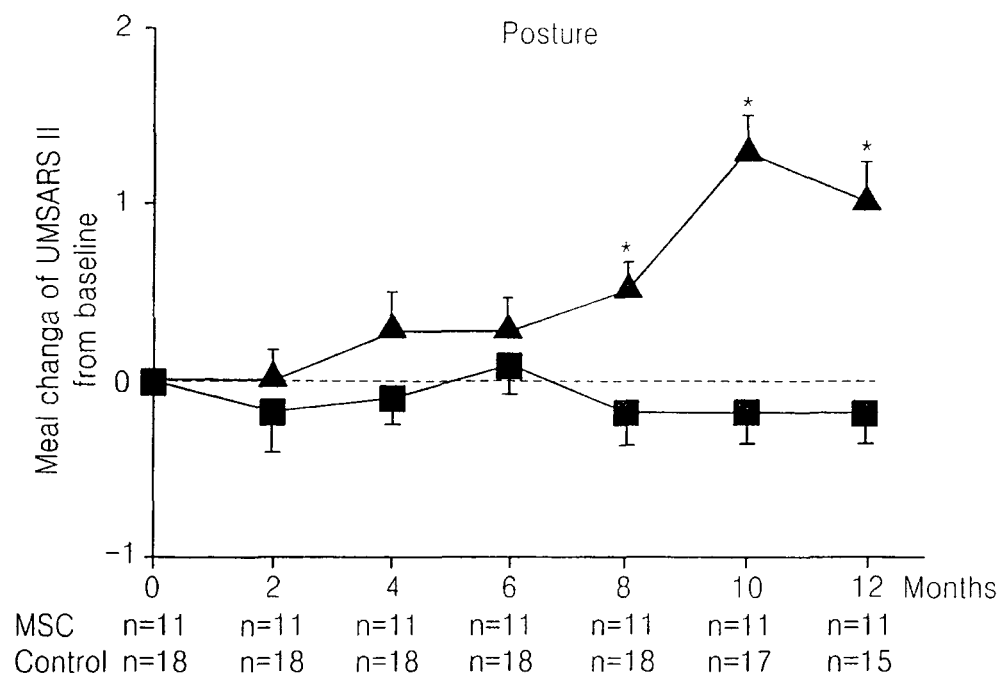
Figure 3:
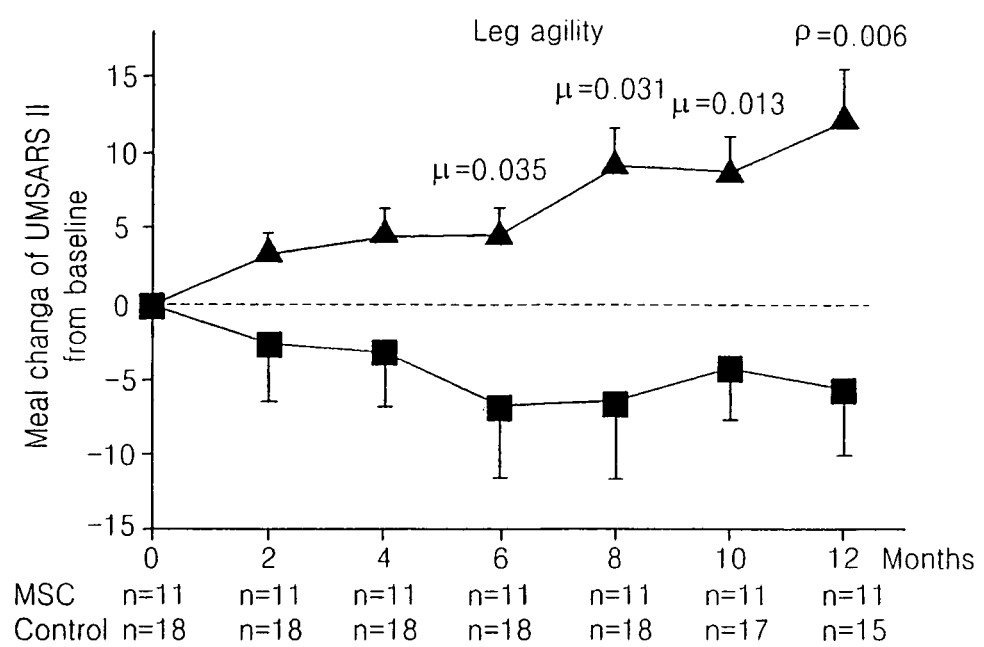
FIG. 3 shows Mean (±SE) change of the UMSARS from baseline in patients with score ranged from 31 to 65. Black squares mean MSC-treated patients and gray triangles mean control patients.

The patients in the MSC group showed significantly greater improvement on the UMSARS than in the control group at all visits throughout the 12-month study period (FIG. 1A). The mean UMSARS score was below baseline severity for the MSC group until 12 months, whereas the scores of the control group increased continuously throughout the study (UMSARS score mean±SE change from baseline at month 12, 14.7±10.4). On analysis of each part of the UMSARS, only UMSARS I showed a significant difference between the two groups from the second visit; this difference was sustained throughout the study (FIG. 1B). On analysis of the individual items in each part of the UMSARS, orthostasis in UMSARS I items and finger tapping, rapid alternating movements, arising from chair, leg agility, and posture among UMSARS II items were statistically different in favor of MSC treatment compared to controls (FIGS. 2A to 2F). To evaluate whether a significant improvement with MSC treatment still existed on comparing two groups with similar baseline scores, we selected MSC-treated (n=5) and control patients (n=14) whose baseline UMSARS score ranged from 31 to 65 (52.5±10.1) in the MSC group and 44.3±11.9 in the control group, P>0.05). A significantly greater improvement on the UMSARS in MSC-treated patients than in control patients was noted from the third visit and was sustained throughout the study (FIG. 3).

Figure 4A:
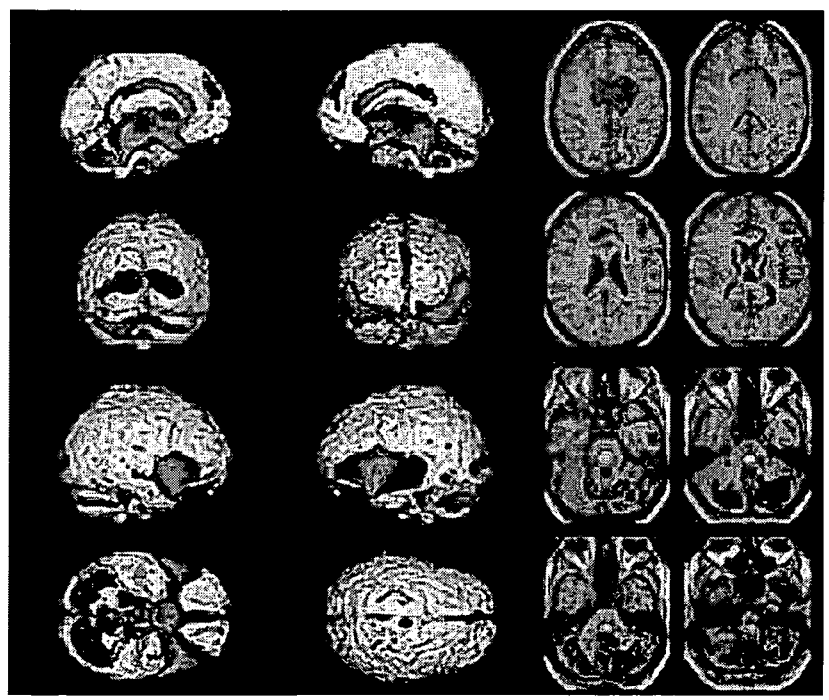
FIGS. 4A and 4B show the change of cerebral glucose metabolism in serial PET scan.
Figure 4B:
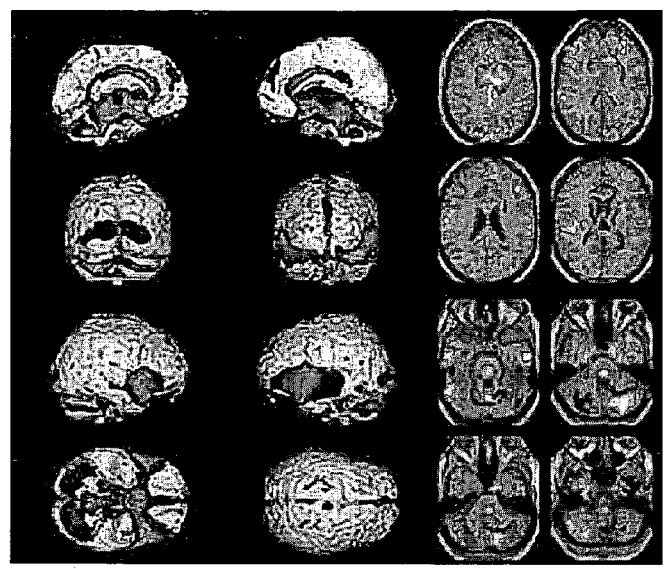

Baseline and follow-up positron emission tomography (PET) data were available for five patients in the MSC group and 10 patients in the control group. The mean follow-up period was 11.9 and 12 months in the MSC and control groups, respectively. In the MSC-treated patients, increased fluorodeoxyglucose (FDG) uptake on the follow-up scan compared to the initial scan was noted in the cerebellum and white matter (FIG. 4A). In contrast, the FDG uptake in the follow-up scan of the control group decreased significantly in the cerebellum and brainstem (FIG. 4B). A list of brain areas in which the change in FDG uptake was significant are illustrated in Tables 2 and 3.

TABLE 2

Brain area showing significant decrease in glucose metabolism on the follow-up PET scan compared to the initial scan in control patients

| | Voxel level | | Talairach |
|---|---|---|---|
| Region | P-value (uncorrected) | Z-score | coordinates x/y/z |
| Left frontal white matter | <0.001 | 4.44 | −6/0/4 |
| Brain stem | <0.001 | 4.27 | 2/−32/−34 |
| Right cerebellum | <0.001 | 4.09 | 8/−38/−10 |
| Both medial frontal gyrus | 0.016 | 2.15 | 0/52/44 |
| Cingulate | 0.045 | 1.70 | 4/52/14 |

In Table 2, PET means positron emission tomography; x means the distance in mm to the right of left (−) of the midline; y means the distance anterior or posterior (−) to the anterior commissure; z means the distance superior or inferior (−) to a horizontal plane through the anterior and posterior commisure.

In Table 2, PET means positron emission tomography; x means the distance in mm to the right or left (−) of the midline; y means the distance anterior or posterior (−) to the anterior commissure; z means the distance superior or inferior (−) to a horizontal plane through the anterior and posterior commissure.

TABLE 3

Brain area showing significant increase in glucose metabolism on the follow-up PET scan compared to the initial scan in MSC-treated patients

| | Voxel level | | Talairach |
|---|---|---|---|
| Region | P-value (uncorrected) | Z-score | coordinates x/y/z |
| Left cerebellum | <0.001 | 3.69 | −40/−34/−38 |
| Left frontal white matter | <0.001 | 3.80 | −30/26/20 |
| Left inferior temporal gyrus | <0.001 | 4.16 | −52/−28/−36 |
| Right frontal white matter | <0.001 | 3.29 | 26/38/2 |
| Right inferior temporal gyrus | 0.004 | 2.62 | 54/−14/−36 |

TABLE 3-continued

Brain area showing significant increase in glucose metabolism on the follow-up PET scan compared to the initial scan in MSC-treated patients

| | Voxel level | | Talairach |
|---|---|---|---|
| Region | P-value (uncorrected) | Z-score | coordinates x/y/z |
| Right cerebellum | 0.006 | 2.51 | 28/−26/−38 |
| Right temporal white matter | 0.018 | 2.09 | 38/−60−14 |

In Table 3, MSC means mesenchymal stem cell; PET means positron emission tomography; x means the distance in mm to the right or left (−) of the midline; y means the distance anterior or posterior (−) to the anterior commissure; z means the distance superior or inferior (−) to a horizontal plane through the anterior and posterior commisure.

In Table 3, MSC means mesenchymal stem cell; PET means positron emission tomography; x means the distance in mm to the right or left (−) of the midline; y means the distance anterior or posterior (−) to the anterior commissure; z means the distance superior or inferior (−) to a horizontal plane through the anterior and posterior commissure.

Figure 5:
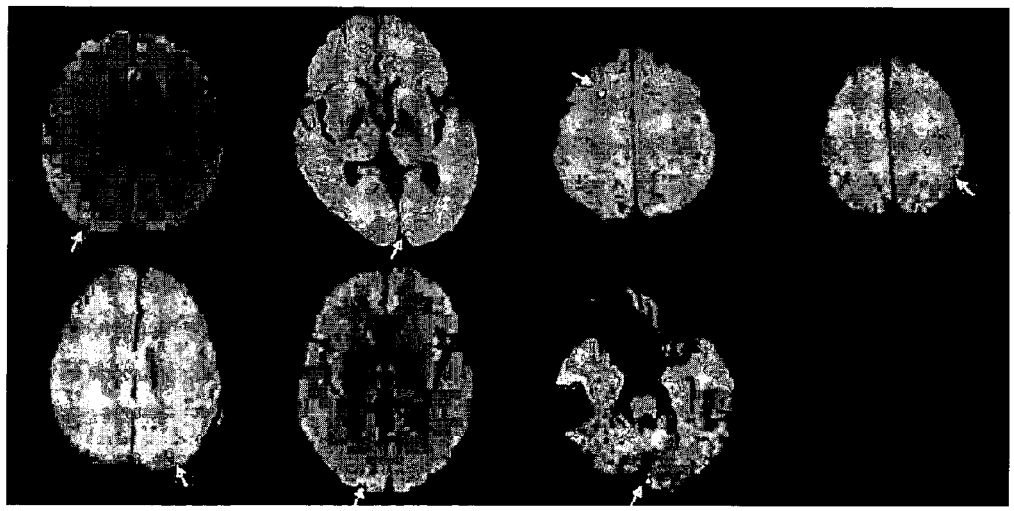
FIG. 5 shows diffusion-weighed MR images performed 1 day after intra-arterial injection of MSCs. Small spotty lesions (<5 mm, white arrow) were observed in seven patients treated with MSCs.

The most common immediate adverse effect after intravenous infusion was fever, which developed in six MSC-treated patients (54.5%). Four patients developed fever during the first and second intravenous infusion, and two patients developed fever during the first intravenous infusion only. The fever responded well to acetaminophen and subsided in 1-3 h. On intra-arterial injection, small spotty lesions (<5 mm) on diffusion-weighted MR images were observed in seven MSC-treated patients (63.6%) without neurological deficits (FIG. 5). Two patients exhibited multiple spotty lesions and five patients had a single lesion. Five patients showed spotty lesions in the territory of the posterior cerebral circulation and two patients had them in the territory of the anterior cerebral circulation. No delayed adverse effects were related to MSC infusion during the 12-month follow-up occurred. One patient developed acute cholecystitis 10 months after MSC infusion; this was caused by previously developed gall bladder stones and was treated with surgical removal.

3. Discussion

The natural course of MSA is relentlessly progressive with a mean survival of 9 years. According to a recent report by the European MSA Study Group, the mean increase in the UMSARS for a mean follow-up period of 12 months was 17.2 points. The annual increase in the UMSARS scores in our control patients was 14.7 points, which is comparable with their results. In contrast, the MSC-treated patients exhibited functional stabilization throughout the study, and functional improvement up to 10 months after cell therapy. These benefits were ascribed to the significant difference in the UMSARS I scores between MSC-treated and control patients. Since the functional deterioration in MSA is more rapid in the early stage of disease rather than at later stages (Geser, F. et al. (2006) Progression of multiple system atrophy (MSA): a prospective natural history study by the European MSA study group (EMSA SG). *Mov. Disord.* 21, 179-186), we conducted a subgroup analysis in which the baseline functional deficits were not significantly different between groups. There was still significantly greater functional improvement in the MSC-treated group than in the controls, suggesting that the functional benefits of MSC therapy do not result from the different functional status between groups, but are attributable to the effect of MSCs.

Although cerebellar, basal ganglia, and white matter derangement constitute the major pathological alterations in MSA, longitudinal imaging study of magnetic resonance imaging or PET is very limited. Recently, Paviour et al. reported in their longitudinal magnetic resonance imaging study that the pons and cerebellum had the highest rates of atrophy in patients with MSA (Paviour, D. C., Price, S. L., Jahanshahi, M., Lees, A. J. & Fox, N. C. (2006) Longitudinal MRI in progressive supranuclear palsy and multiple system atrophy: rates and regions of atrophy. Brain 129, 1040-1049). In this study, we first demonstrated the results of a longitudinal PET study that the FDG uptake in the follow-up scan decreased significantly in the cerebellum and brainstem in patients with MSA, which was well in accordance with the longitudinal magnetic resonance imaging study. In contrast, PET scans in five MSC-treated patients revealed that the increased FDG uptake from the baseline PET scan was most notable in the cerebellum and was also evident in the white matter. We speculate that the increased glucose uptake in these areas may be an effect of MSC therapy and related to clinically functional improvement.

The exact mechanism by which MSC therapy works has yet to be established. MSCs have a variety of properties including the ability to migrate into injury sites, to engraft and disseminate throughout the brain, and to produce various trophic factors that may contribute to functional recovery, neuronal cell survival, and stimulation of endogenous regeneration (Barry, F. P. & Murphy, J. M. (2004) Mesenchymal stem cells: clinical applications and biological characterization. Int. J. Biochem. Cell Biol. 36, 568-584). As suggested by Bang et al. (Bang, O. Y., Lee, J. S., Lee, P. H. & Lee, G. (2005) Autologous mesenchymal stem cell transplantation in stroke patients. Ann. Neurol. 57, 874-882), the mismatch between functional recovery (UMSARS I) and neurological deficits (UMSARS II) implies that the effect of MSCs in our study may be related to the production of trophic factors. However, improvements of neurological deficits in five items of UMSARS II, the prolonged effect of MSC infusion over 12 months, and increased FDG uptake in the follow-up PET scan seen in our study may need other mechanisms besides the transient effects of tropic factors alone. Many studies have clearly shown that MSCs can be induced to differentiate into neurons in vitro with morphological and phenotypic characteristics. Furthermore, pathological studies in bone marrow transplantation recipients demonstrated that MSCs could trans-differentiate into various types of neurons, such as Purkinje cells or hippocampal neurons, although debate is ongoing as to whether these morphological changes are responsible for true trans-differentiation or cell fusion. Recently, Bae et al. demonstrated that MSCs retained the potential to develop into electrically active Purkinje neurons with functional synaptic formation through fusion-like events existing in Purkinje neurons in mice with Niemann-Pick disease type C (Bae, J. S. et al. (2007) Bone marrow-derived mesenchymal stem cells promote neuronal networks with functional synaptic transmission after transplantation into mice with neurodegeneration. Stem Cells 25, 1307-1316). Therefore, it is possible that improvements of cerebellar dysfunction-related items of UMSARS II (rapid alternating movements, arising from chair, and posture) and increased cerebellar metabolism in MSC-treated patients may reflect the functional integration of infused MSCs with host neurons.

We chose intra-arterial infusion and repeated intravenous infusion of MSCs to provide the best opportunity to reach the brain (Amar, A. P., Zlokovic, B. V. & Apuzzo, M. L. (2003) Endovascular restorative neurosurgery: a novel concept for molecular and cellular therapy of the nervous system. Neurosurgery 52, 402-412; discussion 12-13), because the signal for the homing effects of MSCs may be weaker in neurodegenerative disease compared to acute brain insults. Intra-arterial injection in our study was proven to be safe, although it was accompanied by spotty ischemic lesions without neurological deficits. Because the spotty lesions were small and uniform, we speculate that they were related to cell infusion rather than complications of the angiographic procedure. Taking care to dissolve the solution for arterial infusion evenly, we demonstrated that delivery of MSCs through intra-arterial and repeated intravenous route is problem-free.

As this study was an open trial, the functional recovery in MSC-treated patients may be responsible for the placebo effect. The placebo effect might result from the expectation of clinical benefits from a drug or surgical intervention and biochemically be accompanied by the release of dopamine in the nucleus accumbens and the nigrostriatal pathway. According to the study by McRae et al., the expectancy regarding which type of treatment was received had a significant effect, not only on subjective parameters but also on motor examination, and importantly these effects were maintained for 12 months (McRae, C. et al. (2004) Effects of perceived treatment on quality of life and medical outcomes in a double-blind placebo surgery trial. Arch. Gen. Psychiatry 61, 412-420). In our study, the expectancy may be greater because we used an intra-arterial procedure that required a surgical procedure. However, the improvements on cerebellar dysfunction and metabolism observed in the MSC-treated group cannot be solely explained by the placebo effect because cerebellar function is not directly influenced by dopaminergic system, a responsible pathway for the placebo effect. Furthermore, we speculate that the placebo effect may not be sustained for a long time in a rapidly progressive disease condition of MSA.

This study demonstrated that MSC transplantation in patients with MSA delayed the progression of neurological deficits with achievement of functional improvement in the follow-up period, as assessed using the UMSARS. In addition, our study indicated that the procedure of intraarterial infusion and repeated intravenous infusions of MSCs was safe.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for treating multiple system atrophy, comprising administering a therapeutically effective amount of mesenchymal stem cells (MSCs) to a human in need thereof, wherein said MSCs are autologous human mesenchymal stem cells.

2. The method according to claim 1, wherein the administering is performed by an intra-arterial injection of said MSCs and one or more intravenous injections of said MSCs.

3. The method according to claim 2, wherein the intra-arterial injection is performed by infusing MSCs into a bilateral internal carotid artery and/or into a dominant vertebral artery.

4. The method according to claim 3, wherein the intra-arterial injection is performed by infusing about $2 \times 10^7$ MSCs into a bilateral internal carotid artery and about $2 \times 10^7$ MSCs into a dominant vertebral artery for about 60 minutes.

5. The method according to claim 2, wherein the intravenous injections are consecutively performed every month, beginning 1 month after the intra-arterial injection.

6. The method according to claim 5, wherein the intravenous injections are consecutively performed every month for 3 months, beginning 1 month after the intra-arterial injection.

7. The method according to claim 5 or 6, wherein each intravenous injection is performed by infusing about $4 \times 10^7$ MSCs into an antecubital vain for about 30 minutes.

\* \* \* \* \*